United States Patent
Niu et al.

(10) Patent No.: US 12,403,223 B2
(45) Date of Patent: Sep. 2, 2025

(54) METHOD FOR CONSTRUCTING HYDROPHILIC ANTIFOULING COATING ON SURFACE OF MEDICAL IMPLANTABLE MATERIAL

(71) Applicant: Taizhou DOBIOM Medical Devices Co., Ltd., Taizhou (CN)

(72) Inventors: Zhimeng Niu, Taizhou (CN); Qibo Xiao, Taizhou (CN)

(73) Assignee: Taizhou DOBIOM Medical Devices Co., Ltd., Taizhou (CN)

( * ) Notice: Subject to any disclaimer, the term of this patent is extended or adjusted under 35 U.S.C. 154(b) by 0 days.

(21) Appl. No.: 18/724,324

(22) PCT Filed: Jun. 21, 2023

(86) PCT No.: PCT/CN2023/101763
§ 371 (c)(1),
(2) Date: Jun. 26, 2024

(87) PCT Pub. No.: WO2024/051272
PCT Pub. Date: Mar. 14, 2024

(65) Prior Publication Data
US 2024/0424172 A1   Dec. 26, 2024

(30) Foreign Application Priority Data

Sep. 6, 2022 (CN) .......................... 202211086394.8

(51) Int. Cl.
*A61L 29/08* (2006.01)
*A61L 29/06* (2006.01)
*A61L 29/14* (2006.01)

(52) U.S. Cl.
CPC ............. *A61L 29/085* (2013.01); *A61L 29/06* (2013.01); *A61L 29/14* (2013.01); *A61L 2400/18* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 2006/0073207 A1 | 4/2006 | Masters et al. | |
| 2010/0145286 A1 | 6/2010 | Zhang et al. | |
| 2011/0305872 A1 | 12/2011 | Li et al. | |
| 2013/0025764 A1 | 1/2013 | Henderson | |
| 2017/0157298 A1 | 6/2017 | Bernardus et al. | |

FOREIGN PATENT DOCUMENTS

| | | |
|---|---|---|
| CN | 101386684 A | 3/2009 |
| CN | 101455861 A | 6/2009 |
| CN | 102307955 A | 1/2012 |
| CN | 102775831 A | 11/2012 |
| CN | 108815586 A | 11/2018 |
| CN | 108816689 A | 11/2018 |
| CN | 109562202 A | 4/2019 |
| CN | 110804175 A | 2/2020 |
| CN | 115382025 A | 11/2022 |
| WO | 2022019733 A1 | 1/2022 |

OTHER PUBLICATIONS

International Search Report and Written Opinion of corresponding International Application No. PCT/CN2023/101763, mailed on Oct. 12, 2023.
Notification of Grant Patent Right (with translation) issued in Chinese Application No. 202211086394.8 on May 24, 2024.

*Primary Examiner* — Jennifer Chin
(74) *Attorney, Agent, or Firm* — BURR & FORMAN

(57) ABSTRACT

Disclosed is a method for constructing a hydrophilic, antifouling coating on the surface of a medical implantable material. The method comprises the following steps: 1) pretreating the surface of the medical implantable material to obtain a clean surface and/or a hydrophilic active site; and 2) impregnating the medical implantable material that has been pretreated in step 1) in a precursor solution for reaction so as to obtain a reaction interface layer or a free radical reaction and/or polymerization site on the surface of the medical implantable material; and removing the medical implantable material from the solution: 3) carrying out a polymerization grafting reaction; and 4) after the reaction in step 3) is complete, performing a wash and drying, thus finishing the construction of the hydrophilic, antifouling coating on the surface of the medical implantable material. According to the present invention, an alternating-structure amino acid copolymer or a derivative thereof is used as a cross-linking agent to modify the surface of the medical implantable material, and a hydrophilic, antifouling coating is obtained. The coating has relatively good hydrophilicity and in-vivo anti-scaling properties. The hydrophilicity of the coating enables formation of a hydration layer on the surface of the material, facilitating the prevention of protein, bacteria, cells, ions, etc. from adsorption and thus achieving the anti-scaling properties.

6 Claims, 1 Drawing Sheet

METHOD FOR CONSTRUCTING HYDROPHILIC ANTIFOULING COATING ON SURFACE OF MEDICAL IMPLANTABLE MATERIAL

TECHNICAL FIELD

The present invention belongs to the technical field of medical implantable materials, and particularly relates to a method for constructing a hydrophilic antifouling coating on a surface of a medical implantable material

BACKGROUND ART

An implantable urinary catheter/ureteral stent is often needed to be replaced frequently due to the problems such as bacterial infection and catheter blockage during clinical use. For example, infection-related conditions occur in 24% of patients with short-term catheter implantation, which results in a mortality rate of nearly 4%. Fibrin sheaths are formed in ureteral catheters used by at least 42% of the patients implanted with ureteral catheters, and about 20% of these ureteral catheters will develop to form thrombosis, which results in catheter blockage. Scaling and bacterial infection on a surface of the urinary catheter/ureteral stent are main causes of failure in an implantation operation. Bacterial infection may usually promote adsorption of proteins and ions on the surface of the urinary catheter/ureteral stent and formation of fouling. Similarly, fouling can exacerbate bacterial infection. Therefore, it is necessary to modify the surface of the urinary catheter/ureteral stent to solve these problems clinically.

Many researchers have tried to solve the problems of scaling and bacterial adhesion from the perspective of a material surface coating. Coating on an implantable material by zwitterionic polymers, peptides, polyvinylpyrrolidone, etc. is a current main strategy to improve antifouling and antibacterial properties. For example. Cui et al. have polymerized zwitterionic 2-methacryloyloxyethyl phosphorylcholine (MPC) with the antifouling property with a borneol compound with the antibacterial property and of a complex bicyclic monoterpene structure, and then prepared an excellent antifouling and antibacterial surface through a Schiff base. The zwitterionic MPC and borneol play a synergistic role in a copolymer, and play roles of preventing protein adsorption and inhibiting bacterial adhesion respectively through super hydration and a special stereochemical structure. (Cheng. Q . . . et al. Antifouling and Antibacterial Polymer-Coated Surfaces Based on the Combined Effect of Zwitterions and the Natural Borneol. Acs Applied Materials & Interfaces. 2021, 13 (7): 9006-9014.) Although the above strategy solves the problems of preventing scaling and adhesion, and inhibiting bacteria to a certain extent, this method first synthesizes poly (MPC-st-FPMA-st-BA) as a copolymer by reversible addition-fragmentation chain transfer (RAFT), and then modifies a substrate by the Schiff base. The method is tedious. In addition, how to maintain the long-term properties of the modified material during long-term retention after implantation in a body and a low foreign body reaction property during implantation are still difficulties of a research. Therefore, a new method for preparing a surface coating material and a coating is developed to improve resistance of the implant material to scaling and bacterial adhesion, and the modified material has low foreign body reaction property.

SUMMARY OF THE INVENTION

The technical problem to be solved by the present invention is to provide a method for constructing a hydrophilic antifouling coating on a surface of a medical implantable material. The present invention uses an alternating-structure amino acid copolymer or a derivative thereof to modify the surface of the medical implantable material to obtain a coating with hydrophilicity and an antifouling property. This coating has good hydrophilicity and an in vivo anti-scaling property. The hydrophilicity of the coating will form a hydration layer on the surface of the material, which is conducive to blocking adsorption of proteins, bacteria, cells, ions, etc., so as to achieve the anti-scaling property.

To solve the technical problems, the present invention adopts the following technical solution:

A method for constructing a hydrophilic antifouling coating on a surface of a medical implantable material, comprising the following steps:

1) pretreating a surface of a medical implantable material to obtain a clean surface and/or a hydrophilic active site;
2) impregnating the medical implantable material that has been pretreated in step 1) into a precursor solution for a reaction so as to obtain a reaction interface layer or a free radical reaction and/or polymerization site on the surface of the medical implantable material; and taking out the medical implantable material for later use;
3) performing a polymerization grafting reaction
    3.1) after obtaining the reaction interface layer on the surface of the medical implantable material in step 2), placing the medical implantable material in a reaction solution for the polymerization grafting reaction, wherein the reaction solution includes ferrous chloride, ascorbic acid and modified molecules; or
    3.2) after obtaining the free radical reaction and/or polymerization site on the surface of the medical implantable material in step 2), placing the medical implantable material in a reaction solution for the polymerization grafting reaction, wherein the reaction solution comprises a crosslinking agent, the modified molecules and an initiator; and
4) after the reaction in step 3) is completed, performing washing and drying, thus finishing construction of a hydrophilic antifouling coating on the surface of the medical implantable material.

As an implementation, the medical implantable material includes, but is not limited to, the following materials: polyurethane and silica gel.

As an implementation, in step 1), the pretreating mode includes plasma sputtering, ultraviolet irradiation, ozone, washing with a piranha solution, or washing with a sulfuric acid solution.

As a preferred implementation, conditions of treatment with plasma sputtering are as follows: an oxygen atmosphere, and a power of 5-500 W; a condition of treatment with ultraviolet irradiation is 70 $\mu W/cm^2$-9 $W/cm^2$; a condition of treatment with the ozone is 1-100 mg/L: a condition of treatment with the piranha solution is: concentrated sulfuric acid:hydrogen peroxide=7:3 (v/v); and a condition of treatment with the sulfuric acid solution is as follows: a mass percentage concentration is 20-80%.

As an implementation, in step 1), a pretreating time lasts for 1-60 min; and a pretreating temperature is 10-50° C.

As an implementation, in step 2), the precursor solution is a solution for forming a reaction interface layer, or the free radical reaction and/or polymerization site.

As a preferred implementation, the solution for forming the reaction interface layer includes peroxides and the crosslinking agent:

the peroxides are selected from hydrogen peroxide, peroxyacetic acid, tert-butyl hydroperoxide, cumene hydroperoxide;

the crosslinking agent includes one or more of an alternating-structure amino acid copolymer or a derivative thereof, and crosslinking agents containing two or more active sites (such as ethylene dimethacrylate (EGDMA) and phenolic resin); and a mass percentage concentration of the hydrogen peroxide is 1-50%, preferably. 8-20%; a mass percentage concentration of the crosslinking agent is 0.001-50%, preferably, 0.1-30%: a reaction temperature is 10-40° C., preferably, 25-40° C.; and a reaction time lasts for 1-60 min, preferably, 20-30 min.

As a preferred implementation, a solution for forming the free radical reaction and/or polymerization site is a silane coupling agent: the silane coupling agent is selected from one or more of KH550, KH570, and KH792:

a mass percentage concentration of the silane coupling agent is 5-60%, preferably, 10-25%; a reaction temperature is 15-70° C., preferably, 25-40° C.; and a reaction time lasts for 2-8 h. preferably, 3-6 h.

As an implementation, in step 3.1), a mass percentage concentration of the ferrous chloride is 0.01-1.00%, preferably. 0.05-0.5%: a mass percentage concentration of the ascorbic acid is 0.1-10%, preferably, 1-5%: a mass percentage concentration of the modified molecules is 0.1-50%, preferably, 1-30%: a reaction temperature is 10-60° C. preferably, 25-40° C.; and a reaction time lasts for 1-10 h, preferably, 2-6 h.

As an implementation, in step 3.2), a mass percentage concentration of the modified molecules is 0.1-50%, preferably. 1-30%: a mass percentage concentration of the crosslinking agent is 0.001-50%, preferably. 0.1-30%: a reaction temperature is 10-100° C., preferably, 25-70° C.; and a reaction time lasts for 1-10 h, preferably, 3-6 h.

As an implementation, in step 3.2), the crosslinking agent is selected from one or more of the alternating-structure amino acid copolymer or the derivative thereof, and the crosslinking agents containing two or more active sites (such as the ethylene dimethacrylate (EGDMA) and the phenolic resin).

As a preferred implementation, the structural formula of the alternating-structure amino acid copolymer or the derivative thereof is as follows:

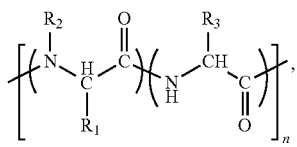

abbreviated as $[AB]_n$, wherein A is

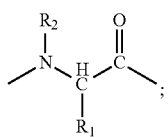

B is

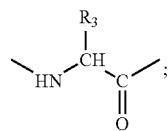

n is an integer; and n=2-10000.

$R_1$ includes, but is not limited to, the following structures:
—$CH_2$—$CH_2$—$CH_2$—$NH_2$,   —$CH_2$—$CH_2$—$NH_2$,
—$CH_2$—$CH_2$—$CH_2$—$CH_2$—$NH_2$, and  —$CH_2$—$CH_2$—NH—CNH—$NH_2$; $R_2$ includes, but is not limited to, the following structures:—H, —$CH_2$—CH—$CH_2$, —$CH_2$—$CH_2$—CH=$CH_2$, $C_6H_5$—$CH_2$—, and —$CH_3$—$C_6H_4$—O—$CH_3$; and $R_5$ includes, but is not limited to, the following structures:—H, —$CH_3$, —$CH_2$—$CH_3$, —$CH_2$—$CH_2$—$CH_3$, —CH—$(CH_3)_2$, —$CH_2$—COOH, —$C(CH_3)_3$, and —$CH_2$—$C_6H_5$.

As an implementation, in step 3.1) and step 3.2), the modified molecules are a hydrophilic substance or a mixture of the hydrophilic substance and the hydrophobic substance.

The hydrophilic substance is one or more of acrylates, zwitterionic substances, polyethylene glycol substances with different molecular weights, or polyvinylpyrrolidone: for example, the hydrophilic substance includes, but is not limited to, one or more of the following substances: 2-hydroxyethyl methacrylate, 2-ethoxyethyl acrylate, poly(ethylene glycol) methyl ether methacrylate (PEGMEM), 2-methacryloyloxyethyl phosphorylcholine (MPC), carboxybetaine, and sulfobetaine; and the hydrophobic substance is one or more of lauryl methacrylate, vinyltrimethylsilane, tert-butyl methacrylate, and cyclohexyl methacrylate.

As an implementation, in step 4), the cleaning is performed with one or more of deionized water, ethyl alcohol, and an SDS solution; and the drying is forced air drying at a temperature of 20-100° C., preferably, 40-80° C.

As a preferred implementation, a mass percentage concentration of the SDS solution is 0.01-1%, preferably, 0.1-0.5%.

Any range recorded by the present invention includes end values, any value between the end values, and an arbitrary sub-range consisting of the end values or any value between the end values.

Unless otherwise noted, the raw materials in the present invention can all be commercially available, and the device used in the present invention can adopt a conventional device in the art or can refer to the prior art in the field.

Compared with the prior art, the present invention has the following beneficial effects that:

1) The alternating-structure amino acid copolymer or the derivative thereof can be used as a new material for constructing the hydrophilic antifouling coating on the surface, and also as a crosslinking agent for compounding with other monomers and/or polymers.

2) By adjusting compositions of two amino acids and derivatives thereof, the alternating-structure amino acid copolymer or the derivative thereof of the present invention is endowed with antibacterial and/or hydrophilic and/or antifouling properties, so as to jointly construct a functional coating with other monomers and/or polymers, which effectively prevents formation of scaling and bacterial adhesion.

BRIEF DESCRIPTION OF THE DRAWINGS

The specific implementations of the present invention will be described below in detail with reference to the accompanying drawings.

DETAILED DESCRIPTION OF THE INVENTION

Figure 1:
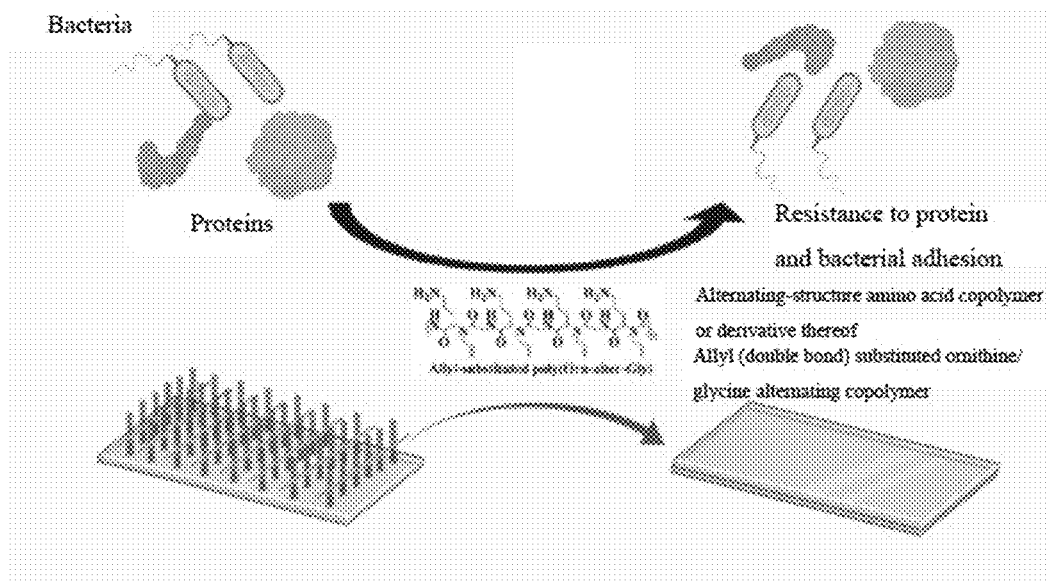
FIG. 1 is a schematic diagram of an antifouling property of a coating on a surface of the present invention.

For more clearly illustrating the present invention, the following are further descriptions of the present invention with reference to preferred embodiments. Those skilled in the art would understand that the following concretely described content is intended to be illustrative and not limiting, which should not be construed to limit the scope of the present invention.

It should be noted that, when an element is referred to as being "fixed to" or "arranged on" another element, it can be directly on or indirectly on the other element. When an element is referred to as being "connected to" another element, it can be directly or indirectly connected to the other element.

It should be noted that, in description of the invention, it should be understood that orientations or positional relationships indicated by terms "length", "width", "upper", "lower", "front", "rear", "left", "right", "vertical", "horizontal", "top", "bottom", "inner". "outer" and the like are based on orientations or positional relationships shown in the drawings, are to facilitate the description of the utility model and simplify the description merely, do not indicate or imply that the referred apparatuses or elements must have specific orientations and are constructed and operated in the specific orientations and thus should not be construed to limit the invention.

In addition, the terms "first". "second" are used only for description and shall not be interpreted as an indication or implication of relative importance or an implicit indication of the number of technical features. Thus, features defined with "first", "second" may include at one or more such features, either explicitly or implicitly. In the description of the invention. "a plurality of" means two or more, unless otherwise specifically defined.

In an aspect of the present invention, the present invention provides a method for constructing a hydrophilic antifouling coating on a surface of a medical implantable material, including the following steps:

1) pretreating a surface of a medical implantable material to obtain a clean surface and/or a hydrophilic active site;

2) impregnating the medical implantable material that has been pretreated in step 1) in a precursor solution for a reaction so as to obtain a reaction interface layer or a free radical reaction and/or polymerization site on the surface of the medical implantable material; and taking out the medical implantable material for later use;

3) performing a polymerization grafting reaction 3.1) after obtaining the reaction interface layer on the surface of the medical implantable material in step 2), placing the medical implantable material in a reaction solution for the polymerization grafting reaction, wherein the reaction solution includes ferrous chloride, ascorbic acid and modified molecules; or 3.2) after obtaining the free radical reaction and/or polymerization site on the surface of the medical implantable material in step 2), placing the medical implantable material in a reaction solution for the polymerization grafting reaction, wherein the reaction solution includes a crosslinking agent, the modified molecules and an initiator; and 4) after the reaction in step 3) is completed, performing washing and drying, thus finishing construction of a hydrophilic antifouling coating on the surface of the medical implantable material.

In certain embodiments of the present invention, the medical implantable material includes, but is not limited to, the following materials: polyurethane or silica gel.

In certain embodiments of the present invention, in step 1), the pretreating mode includes plasma sputtering, ultraviolet irradiation, ozone, and washing with a piranha solution or a sulfuric acid solution. The first purpose of the pretreating is to clean the surface of the material. The second purpose of the pretreating is to successfully perform subsequent steps. Such medical material for the implantable catheter/ureteral stent is a polymer material. After cleaning treatment, a hydroxyl-rich surface is formed on the surface, and is a hydrophilic surface, which is conducive to a subsequent reaction in step 2).

In certain embodiments of the present invention, conditions of treatment with plasma sputtering are as follows: an oxygen atmosphere, and a power of 5-500 W: a condition of treatment with ultraviolet irradiation is 70 $\mu W/cm^2$-9 $W/cm^2$: a condition of treatment with the ozone is 1-100 mg/L: a condition of treatment with the piranha solution is: concentrated sulfuric acid:hydrogen peroxide=7:3 (v/v); and a condition of treatment with the sulfuric acid solution is as follows: a mass percentage concentration is 20-80%. Plasma sputtering and ultraviolet irradiation may cause unsatisfactory results due to too high or too low power, or a too large irradiation area.

A proportion of the piranha solution is concentrated sulfuric acid:hydrogen peroxide=7:3 (v/v); and the hydrogen peroxide and the concentrated sulfuric acid jointly play a role of oxidative cleaning. The sulfuric acid solution is concentrated sulfuric acid solutions with different concentrations: the higher a content of the concentrated sulfuric acid is, the stronger the oxidation is; but it may cause a damage on the substrate, so the sulfuric acid solution at a certain concentration is more suitable.

In certain embodiments of the present invention, in step 1), a pretreating time lasts for 1-60 min; and a pretreating temperature is 10-50° C. A duration of the time and a temperature level may both change the properties of the substrate, such as an appearance color, a mechanical property, and a surface structure, and may even damage the substrate.

In certain embodiments of the present invention, in step 2), the precursor solution is a solution for forming the reaction interface layer, or the free radical reaction and/or polymerization site. Both formation of the interface layer and the reaction site essentially produce free radicals, to provide a free radical reaction site for the subsequent free radical reaction or free radical polymerization.

In certain embodiments of the present invention, the solution for forming the reaction interface layer includes peroxides and the crosslinking agent:

the peroxides are selected from hydrogen peroxide, peroxyacetic acid, tert-butyl hydroperoxide, cumene hydroperoxide;

the crosslinking agent includes one or more of an alternating-structure amino acid copolymer or a derivative thereof, and ethylene dimethacrylate (EGDMA); and a mass percentage concentration of the hydrogen peroxide is 1-50%, preferably, 8-20%;

a mass percentage concentration of the crosslinking agent is 0.001-50%, preferably, 1-30%; a reaction temperature is 10-40° C., preferably, 25-40° C.; and a reaction time lasts for 1-60 min, preferably, 20-30 min.

In certain embodiments of the present invention, a solution for forming the free radical reaction and/or polymerization site is a silane coupling agent: the silane coupling agent is selected from one or more of KH550, KH570, and KH792:

a mass percentage concentration of the silane coupling agent is 5-60%, preferably, 10-25%; a reaction temperature is 15-70° C., preferably, 25-40° C.; and a reaction time lasts for 2-8 h, preferably, 3-6 h.

In certain embodiments of the present invention, in step 3.1), a mass percentage concentration of the ferrous chloride is 0.01-1.00%, preferably, 0.05-0.5%: a mass percentage concentration of the ascorbic acid is 0.1-10%, preferably, 1-5%: a mass percentage concentration of the modified molecules is 0.1-50%, preferably, 1-30%: a reaction temperature is 10-60° C., preferably, 25-40° C.; and a reaction time lasts for 1-10 h, preferably, 2-6 h.

In certain embodiments of the present invention, in step 3.2), a mass percentage concentration of the modified molecules is 0.1-50%, preferably, 1-30%: a mass percentage concentration of the crosslinking agent is 0.001-50%, preferably, 1-30%: a reaction temperature is 10-100° C., preferably, 25-70° C.; and a reaction time lasts for 1-10 h, preferably, 3-6 h.

In certain embodiments of the present invention, in step 3.2), the crosslinking agent is selected from one or more of the alternating-structure amino acid copolymer or the derivative thereof, and the crosslinking agents containing two or more active sites (such as the ethylene dimethacrylate (EGDMA) and phenolic resin).

In certain embodiments of the present invention, the structural formula of the alternating-structure amino acid copolymer or the derivative thereof is as follows:

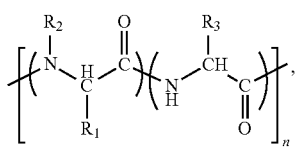

abbreviated as [AB]$_n$, wherein A is

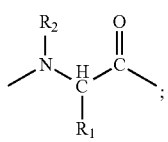

B is

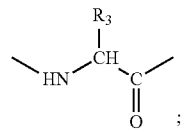

n is an integer; and n=2-10000.

R$_1$ includes, but is not limited to, the following structures: —CH$_2$—CH$_2$—CH$_2$—NH$_2$, —CH$_2$—CH$_2$—NH$_2$, —CH$_2$—CH$_2$—CH$_2$—CH$_2$—NH$_2$, and —CH$_2$—CH$_2$—NH—CNH—NH$_2$; R$_2$ includes, but is not limited to, the following structures: —H, —CH$_2$—CH=CH$_2$, —CH$_2$—CH$_2$—CH=CH$_2$, C$_6$H$_5$—CH$_2$—, and —CH$_3$—C$_6$H$_4$—O—CH$_3$; and R$_5$ includes, but is not limited to, the following structures:—H, —CH$_3$, —CH$_2$—CH$_3$, —CH$_2$—CH$_2$—CH$_3$, —CH—(CH$_3$)$_2$, —CH$_2$—COOH, —C(CH$_3$)$_3$, and —CH$_2$—C$_6$H$_5$.

In certain embodiments of the present invention, in step 3.1) and step 3.2), the modified molecules are a hydrophilic substance or a mixture of the hydrophilic substance and a hydrophobic substance.

The hydrophilic substance is one or more of acrylates, zwitterionic substances, polyethylene glycol substances with different molecular weights, or polyvinylpyrrolidone: for example, the hydrophilic substance includes, but is not limited to, one or more of the following substances: 2-hydroxyethyl methacrylate, 2-ethoxyethyl acrylate, poly(ethylene glycol) methyl ether methacrylate (PEGMEM), 2-methacryloyloxyethyl phosphorylcholine (MPC), carboxybetaine, and sulfobetaine; and the hydrophobic substance is one or more of lauryl methacrylate, vinyltrimethylsilane, tert-butyl methacrylate, and cyclohexyl methacrylate.

In certain embodiments of the present invention, in step 4), the cleaning is performed with one or more of deionized water, ethyl alcohol, and an SDS solution; and the drying is forced air drying at a temperature of 20-100° C., preferably, 40-80° C.

In certain embodiments of the present invention, a mass percentage concentration of the SDS solution is 0.01-1%, preferably, 0.1-0.5%.

Embodiment 1

A method for constructing a hydrophilic antifouling coating on a surface of a medical polyurethane sheet includes the following steps:

Pretreating a 1 cm×1 cm polyurethane sheet with a 60% sulfuric acid solution for 1 h; washing the polyurethane sheet, and then impregnating the polyurethane sheet into a 10% KH570 solution at 37° C. for a reaction for 6 h; and placing the polyurethane sheet formed with a free radical polymerization site in a solution containing 20% allyl-substituted ornithine/glycine alternating copolymer and a 0.5% ammonium persulfate for a reaction at 70° C. for 4 h. Washing the polyurethane sheet with deionized water and ethyl alcohol for three times respectively, and drying the polyurethane sheet at 60° C. for 2 h.

The structural formula of an alternating-structure amino acid copolymer or a derivative thereof in this embodiment is as follows:

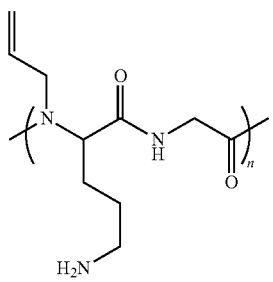

wherein n=4-30.

Embodiment 2

A method for constructing a hydrophilic antifouling coating on a surface of a medical polyurethane sheet includes the following steps:

Pretreating a 1 cm×1 cm polyurethane sheet with a 60% sulfuric acid solution for 1 h; washing the polyurethane sheet, and then impregnating the polyurethane sheet into a 10% KH570 solution at 37° C. for a reaction for 6 h; and placing the polyurethane sheet formed with a free radical polymerization site in a solution containing 10% omnithine/serine alternating copolymer and a 0.5% ammonium persulfate for a reaction at 70° C. for 4 h. Washing the polyurethane sheet with deionized water and ethyl alcohol for three times respectively, and drying the polyurethane sheet at 60° C. for 2 h.

The structural formula of an alternating-structure amino acid copolymer or a derivative thereof in this embodiment is as follows:

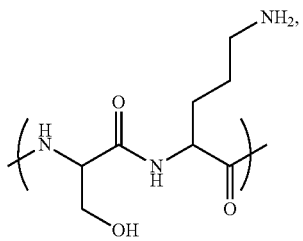

wherein n=2-38.

Embodiment 3

A method for constructing a hydrophilic antifouling coating on a surface of a medical ureteral stent includes the following steps:

Cleaning a 6 cm ureteral stent with a 60% sulfuric acid solution for 1 h; washing the ureteral stent, and then impregnating the ureteral stent into a 10% KH570 solution at 37° C. for a reaction for 4 h; and placing the ureteral stent formed with a free radical polymerization site in a solution containing an allyl-substituted ornithine/glycine alternating copolymer, 2-methacryloyloxyethyl phosphorylcholine, and ammonium persulfate as an initiator for a reaction at 70° C. for 4 h, wherein a molar ratio of the allyl-substituted ornithine/glycine alternating copolymer to the 2-methacryloyloxyethyl phosphorylcholine is 6:4 (with a total mass percentage concentration of 10%), and a concentration of the ammonium persulfate is 0.5%. Washing the ureteral stent with water and ethyl alcohol for three times respectively, and drying the ureteral stent at 60° C. for 2 h. All the prepared samples are subjected to scaling tests in animals. Scaling conditions are shown in FIG. 3.

The structural formula of the alternating-structure amino acid copolymer or the derivative thereof in this embodiment is as follows:

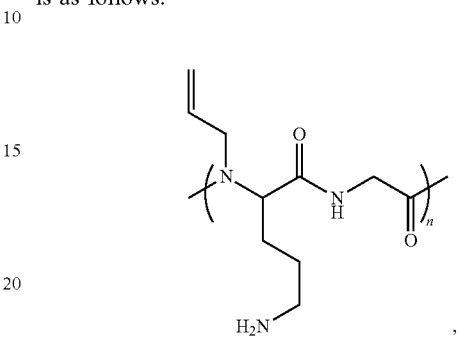

wherein n=4-30.

Embodiment 4

A method for constructing a hydrophilic antifouling coating on a surface of a medical polyurethane tube includes the following steps:

Pretreating a 1 cm polyurethane tube with a 60% sulfuric acid solution for 30 min; washing the polyurethane tube, and then impregnating the polyurethane tube into a 10% KH570 solution at 37° C. for a reaction for 2 h; and placing the polyurethane tube formed with a free radical polymerization site in a solution containing 2-methacryloyloxyethyl phosphorylcholine, 2-hydroxyethyl methacrylate, lauryl methacrylate, allyl-substituted ornithine/glycine alternating copolymer, and 1% azodiisobutyronitrile for a reaction at 70° C. for 4 h, wherein a ratio of the 2-methacryloyloxyethyl phosphorylcholine, the 2-hydroxyethyl methacrylate, the lauryl methacrylate, and the allyl-substituted omnithine/glycine alternating copolymer is 60:25:10:5, with a total mass percentage of 6%. Washing the polyurethane tube with deionized water and ethyl alcohol for three times respectively, and drying the polyurethane tube at 60° C. for 2 h.

The structural formula of an alternating-structure amino acid copolymer or a derivative thereof in this embodiment is as follows:

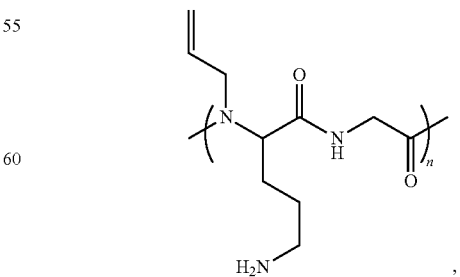

wherein n=4-30.

Embodiment 5

A method for constructing a hydrophilic antifouling coating on a surface of a medical ureteral stent includes the following steps:

Pretreating a 6 cm polyurethane tube with a 60% sulfuric acid solution for 1 h; washing the polyurethane tube, and then impregnating the polyurethane tube into a 10% KH570 solution at 37° C. for a reaction for 2 h; and placing the polyurethane tube formed with a free radical polymerization site in a solution containing 10% 2-methacryloyloxyethyl phosphorylcholine, a 5% allyl-substituted ornithine/glycine alternating copolymer as a crosslinking agent, and 0.1% ammonium persulfate as an initiator for a reaction at 70° C. for 4 h. Washing the polyurethane tube with deionized water for three times, and drying the polyurethane tube at 80° C. for 1 h.

The structural formula of an alternating-structure amino acid copolymer or a derivative thereof in this embodiment is as follows:

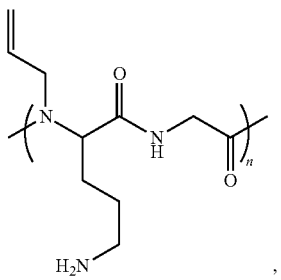

wherein n=4-30.

Embodiment 6

Figure 2:
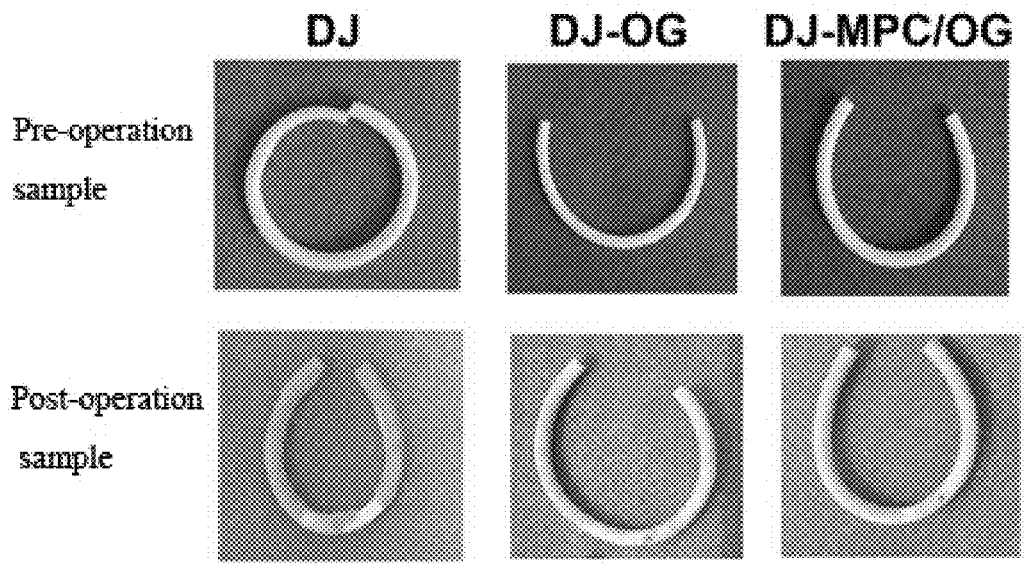
FIG. 2 shows in vivo scaling conditions of prepared samples with modified and unmodified surfaces in embodiment 3.

A method for constructing a hydrophilic antifouling coating on a surface of a medical polyurethane sheet includes the following steps:

Immersing a 1 cm×1 cm polyurethane sheet into a 40% sulfuric acid solution for cleaning treatment for 1 h; washing the polyurethane sheet, and then impregnating the polyurethane sheet into a mixed solution of 20% cumene hydroperoxide and 10% EGDMA at 25° C. for a reaction for 20 min; and placing the polyurethane sheet formed with an interface layer in a solution containing 0.1% ferrous chloride, 1% ascorbic acid, 1.75% PEG with a molecular weight of 20000, and 4% 2-methacryloyloxyethyl phosphorylcholine (MPC) for a reaction at 25° C. for 2 h. Washing the polyurethane sheet with water and ethyl alcohol for three times respectively, and drying the polyurethane sheet at 60° C. for 2 h. A hydrophilic test is performed on the dried samples. Results are shown in FIG. 2, showing better hydrophilicity of the modified samples.

Embodiment 7

A method for constructing a hydrophilic antifouling coating on a surface of a medical polyurethane sheet includes the following steps:

Immersing a 1 cm×1 cm polyurethane sheet into a 40% sulfuric acid solution for cleaning treatment for 1 h; washing the polyurethane sheet, and then impregnating the polyurethane sheet into a mixed solution of 20% cumene hydroperoxide, 10% EGDMA, and 1% ornithine/glycine alternating copolymer at 25° C. for a reaction for 20 min; and placing the polyurethane sheet formed with an interface layer in a solution containing 0.1% ferrous chloride, 1% ascorbic acid, 1.75% PEG with a molecular weight of 20000, and 4% 2-methacryloyloxyethyl phosphorylcholine (MPC) for a reaction at 25° C. for 2 h. Washing the polyurethane sheet with water and ethyl alcohol for three times respectively, and drying the polyurethane sheet at 60° C. for 2 h.

The structural formula of an alternating-structure amino acid copolymer or a derivative thereof in this embodiment is as follows:

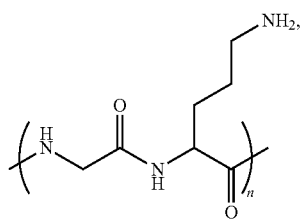

wherein n=2-50.

Embodiment 8

A method for constructing a hydrophilic antifouling coating on a surface of a medical polyurethane sheet includes the following steps:

Immersing a 1 cm×1 cm polyurethane sheet into a 40% sulfuric acid solution for cleaning treatment for 1 h; washing the polyurethane sheet, and then impregnating the polyurethane sheet into a mixed solution of 20% cumene hydroperoxide, 10% EGDMA, and 1% ornithine/valine alternating copolymer at 25° C. for a reaction for 20 min; and placing the polyurethane sheet formed with an interface layer in a solution containing 0.1% ferrous chloride, 1% ascorbic acid, 1.75% PEG with a molecular weight of 20000, and 4% 2-methacryloyloxyethyl phosphorylcholine (MPC) for a reaction at 25° C. for 2 h. Washing the polyurethane sheet with water and ethyl alcohol for three times respectively, and drying the polyurethane sheet at 60° C. for 2 h.

The structural formula of an alternating-structure amino acid copolymer or a derivative thereof in this embodiment is as follows:

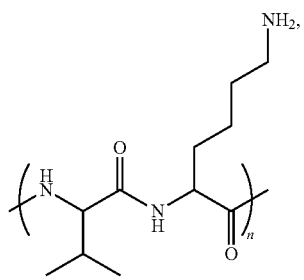

wherein n=2-45.

Embodiment 9

A method for constructing a hydrophilic antifouling coating on a surface of a medical polyurethane sheet includes the following steps:

Immersing a 1 cm×1 cm polyurethane sheet into a 40% sulfuric acid solution for cleaning treatment for 1 h; washing the polyurethane sheet, and then impregnating the polyurethane sheet into a mixed solution of 20% cumene hydroperoxide and 1% ornithine/glycine alternating copolymer at 25° C. for a reaction for 20 min; and placing the polyurethane sheet formed with an interface layer in a solution containing 0.1% ferrous chloride, 1% ascorbic acid, 1.75% PEG with a molecular weight of 20000, and 4% 2-methacryloyloxyethyl phosphorylcholine (MPC) for a reaction at 25° C. for 2 h. Washing the polyurethane sheet with water and ethyl alcohol for three times respectively, and drying the polyurethane sheet at 60° C. for 2 h.

The structural formula of an alternating-structure amino acid copolymer or a derivative thereof in this embodiment is as follows:

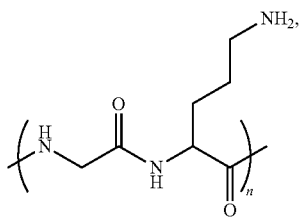

wherein n=2-50.

Embodiment 10

A method for constructing a hydrophilic antifouling coating on a surface of a medical ureteral stent includes the following steps:

Pretreating a 6 cm polyurethane tube with a 60% sulfuric acid solution for 1 h; washing the polyurethane tube, and then impregnating the polyurethane tube into a 10% KH570 solution at 37° C. for a reaction for 2 h; and placing the polyurethane tube formed with a free radical polymerization site in a solution containing 2-methacryloyloxyethyl phosphorylcholine, poly(ethylene glycol) methyl ether methacrylate (PEGMEM), ethylene dimethacrylate (EGDMA), and 0.1% ammonium persulfate as an initiator for a reaction at 70° C. for 4 h, wherein a ratio of the 2-methacryloyloxyethyl phosphorylcholine, the poly(ethylene glycol) methyl ether methacrylate (PEGMEM), and the ethylene dimethacrylate (EGDMA) is 90:5:5, with a total mass percentage of 4%. Washing the polyurethane tube with deionized water for three times, and drying the polyurethane tube at 80° C. for 1 h.

Embodiment 11

A method for constructing a hydrophilic antifouling coating on a surface of a medical ureteral stent includes the following steps:

Pretreating a 6 cm polyurethane tube with a 60% sulfuric acid solution for 1 h; washing the polyurethane tube, and then impregnating the polyurethane tube into a 10% KH570) solution at 37° C. for a reaction for 2 h; and placing the polyurethane tube formed with a free radical polymerization site in a solution containing 2-methacryloyloxyethyl phosphorylcholine, poly(ethylene glycol) methyl ether methacrylate (PEGMEM), an allyl-substituted ornithine/glycine alternating copolymer, and 0.1% ammonium persulfate as an initiator for a reaction at 70° C. for 4 h, wherein a ratio of the 2-methacryloyloxyethyl phosphorylcholine, the poly(ethylene glycol) methyl ether methacrylate (PEGMEM), and the allyl-substituted ornithine/glycine alternating copolymer is 90:5:5, with a total mass percentage of 4%. Washing the polyurethane tube with deionized water for three times, and drying the polyurethane tube at 80° C. for 1 h.

The structural formula of an alternating-structure amino acid copolymer or a derivative thereof in this embodiment is as follows:

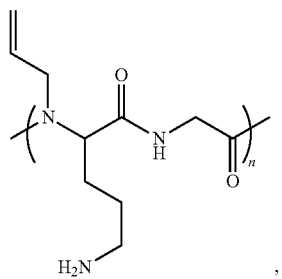

wherein n=4-30.

Embodiment 12

A method for constructing a hydrophilic antifouling coating on a surface of a medical ureteral stent includes the following steps:

Pretreating a 6 cm polyurethane tube with a 60% sulfuric acid solution for 1 h; washing the polyurethane tube, and then impregnating the polyurethane tube into a 10% KH570 solution at 37° C. for a reaction for 2 h; and placing the polyurethane tube formed with a free radical polymerization site in a solution containing 2-methacryloyloxyethyl phosphorylcholine, poly(ethylene glycol) methyl ether methacrylate (PEGMEM), ethylene dimethacrylate (EGDMA), an allyl-substituted ornithine/glycine alternating copolymer, and 0.1% ammonium persulfate as an initiator for a reaction at 70° C. for 4 h, wherein a ratio of the 2-methacryloyloxyethyl phosphorylcholine, the poly(ethylene glycol) methyl ether methacrylate (PEGMEM), the ethylene dimethacrylate (EGDMA), and the allyl-substituted ornithine/glycine alternating copolymer is 85:5:5:5, with a total mass percentage of 4%. Washing the polyurethane tube with deionized water for three times, and drying the polyurethane tube at 80° C. for 1 h.

The structural formula of an alternating-structure amino acid copolymer or a derivative thereof in this embodiment is as follows:

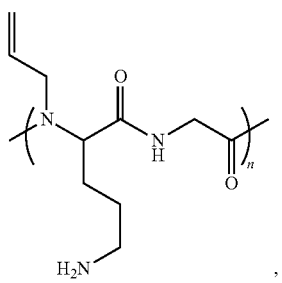

wherein n=4-30.

Embodiment 13

A method for constructing a hydrophilic antifouling coating on a surface of a medical polyurethane sheet includes the following steps:

Pretreating a 1 cm×1 cm polyurethane sheet with a 60% sulfuric acid solution for 1 h; washing the polyurethane sheet, and then impregnating the polyurethane sheet into a 10% KH570 solution at 37° C. for a reaction for 2 h; and placing the polyurethane sheet formed with a free radical polymerization site in a solution containing 2-methacryloyloxyethyl phosphorylcholine, 2-hydroxyethyl methacrylate, lauryl methacrylate, ethylene dimethacrylate (EGDMA), and 1% azodiisobutyronitrile as an initiator for a reaction at 70° C. for 4 h, wherein a ratio of the 2-methacryloyloxyethyl phosphorylcholine, the 2-hydroxyethyl methacrylate, the lauryl methacrylate, and the ethylene dimethacrylate (EGDMA) is 70:20:5:5, with a total mass percentage of 8%. Washing the polyurethane sheet with deionized water and a 0.1% SDS solution for three times respectively, and drying the polyurethane sheet at 80° C. for 1 h.

Embodiment 14

A method for constructing a hydrophilic antifouling coating on a surface of a medical polyurethane sheet includes the following steps:

Pretreating a 1 cm×1 cm polyurethane sheet with a 60% sulfuric acid solution for 1 h; washing the polyurethane sheet, and then impregnating the polyurethane sheet into a 10% KH570 solution at 37° C. for a reaction for 2 h; and placing the polyurethane sheet formed with a free radical polymerization site in a solution containing 2-methacryloyloxyethyl phosphorylcholine, 2-hydroxyethyl methacrylate, lauryl methacrylate, allyl-substituted ornithine/glycine alternating copolymer, and 1% azodiisobutyronitrile as an initiator for a reaction at 70° C. for 4 h, wherein a ratio of the 2-methacryloyloxyethyl phosphorylcholine, the 2-hydroxyethyl methacrylate, the lauryl methacrylate, and the allyl-substituted ornithine/glycine alternating copolymer is 70:20:5:5, with a total mass percentage of 8%. Washing the polyurethane sheet with deionized water and a 0.1% SDS solution for three times respectively, and drying the polyurethane sheet at 80° C. for 1 h.

The structural formula of an alternating-structure amino acid copolymer or a derivative thereof in this embodiment is as follows:

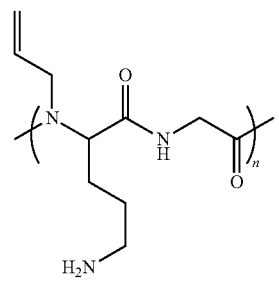

wherein n=4-30.

Comparative Example 1

This comparative example is different from embodiment 1 only in that:

In a case that the mass percentage concentration of the allyl-substituted omnithine/glycine alternating copolymer is smaller than 0.001%, the material has weaker antibacterial property, and cannot have the antibacterial property while being hydrophilic and antifouling.

Comparative Example 2

This comparative example is different from embodiment 2 only in that:

In a case that a time of the polymerization grafting reaction at 70° C. lasts for less than 1 h, the reaction is insufficient, and an amount of polymerization grafting is smaller.

Comparative Example 3

This comparative example is different from embodiment 3 only in that:

In a case that a cleaning time lasts for less than 1 min, cleaning is insufficient, which results in nonuniformity of subsequent polymerization grafting.

Comparative Example 4

This comparative example is different from embodiment 4 only in that:

In a case that a temperature of polymerization grafting reaction is 110° C., there will be changes on appearance and morphology of the material.

Comparative Example 5

This comparative example is different from embodiment 5 only in that:

In a case that the mass percentage concentration of the sulfuric acid during pretreating is increased to 85%, there will be larger deformation on the material.

Comparative Example 6

This comparative example is different from embodiment 6 that:

In a case that the mass percentage concentration of a silane coupling agent KH570 is increased to 65%, increase in a crosslinking degree in the solution affects production of the active site on the surface.

Comparative Example 7

This comparative example is different from embodiment 7 that:

In a case that the mass percentage concentration of the ethylene dimethacrylate (EGDMA) as the crosslinking agent is lowered to 0.001%, a crosslinking degree is weaker, which is not conductive to polymerization of the modified molecules on the surface.

Comparative Example 8

This comparative example is different from embodiment 8 that:

In a case that the mass percentage concentration of the crosslinking agent EGDMA is increased to 55%, the crosslinking degree in the solution will become larger, and the solution is changed into a gel state finally, which is not conductive to modification of the surface of the material.

Comparative Example 9

This comparative example is different from embodiment 9 that:

In a case that the mass percentage concentration of the 2-methacryloyloxyethyl phosphorylcholine as the modified molecules is lowered to 0.05%, modification of the surface of the material is insufficient, and the hydrophilicity of the surface of the material is weaker.

Comparative Example 10

This comparative example is different from embodiment 10 that:

In a case that a drying temperature is 110° C., there will be changes on appearance and morphology of the material.

Comparative Example 11

This comparative example is different from embodiment 11 that:

In a case that a temperature of the polymerization grafting reaction is 5° C., the grafting reaction is slow in rate, and is insufficient.

Comparative Example 12

This comparative example is different from embodiment 12 that:

In a case that a temperature of silicane coupling is 90° C., a solvent is volatile, which results in uneven grafting.

Comparative Example 13

This comparative example is different from embodiment 13 that:

In a case of a concentration of KH570 being 1%, pretreating on the surface is uneven.

Comparative Example 14

This comparative example is different from embodiment 14 that:

In a case that a concentration of the allyl-substituted ornithine/glycine alternating copolymer is smaller than 0.01%, the material is low in crossing degree, and has poorer antibacterial property.

Apparently, the above-described embodiments of the present invention are merely clear illustrations of examples of the present invention and are not limitation to the implementations of the present invention. To those of ordinary skill in the art, other changes or variations in different forms may also be made on the bases of the description. All the implementations cannot be exhaustive here. The apparent changes or variations extended by the technical solution of the present invention all remain within the scope of protection of the present invention.

The invention claimed is:

1. A method for constructing a hydrophilic antifouling coating on a surface of a medical implantable material, comprising the following steps:

1) pretreating a surface of a medical implantable material to obtain a pretreated surface and/or a hydrophilic active site;

2) impregnating the medical implantable material that has been pretreated in step 1) in a precursor solution for a reaction so as to obtain a free radical reaction and/or polymerization site on the surface of the medical implantable material; and taking out the medical implantable material for later use;

3) performing a polymerization grafting reaction after obtaining the free radical reaction and/or polymerization site on the surface of the medical implantable material in step 2), placing the medical implantable material in a reaction solution for the polymerization grafting reaction, wherein the reaction solution comprises a crosslinking agent, modified molecules and an initiator; and 4) after the reaction in step 3) is completed, performing washing and drying, thus finishing construction of a hydrophilic antifouling coating on the surface of the medical implantable material, wherein in step 3), a mass percentage concentration of the modified molecules is 0.1-50%; a mass percentage concentration of the crosslinking agent is 0.001-50%; a reaction temperature is 10-100° C.; and a reaction time lasts for 1-10 h;

in step 3), the crosslinking agent is selected from an alternating-structure amino acid copolymer;

the structural formula of the alternating-structure amino acid copolymer is as follows:

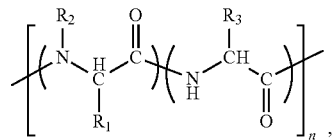

abbreviated as $[AB]_n$, wherein A is

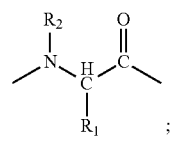

B is

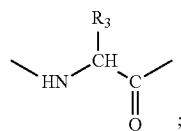

n is an integer; and n=2-10000;

R₁ comprises the following structures: $-CH_2-CH_2-CH_2-NH_2$, $-CH_2-CH_2-NH_2$, $-CH_2-CH_2-CH_2-CH_2-NH_2$, and $-CH_2-CH_2-NH-CNH-NH_2$; $R_2$ comprises the following structures: $-H$, $-CH_2-CH-CH_2$, $-CH_2-CH_2-CH-CH_2$, $C_6H_5-CH_2-$, and $-CH_3-C_6H_4-O-CH_3$; and $R_3$ comprises the following structures: $-H$, $-CH_3$, $-CH_2-CH_3$, $-CH_2-CH_2-CH_3$, $-CH-(CH_3)_2$, $-CH_2-COOH$, $-C(CH_3)_3$, and $-CH_2-C_6H_5$;

in step 3), the modified molecules are a hydrophilic substance or a mixture of the hydrophilic substance and a hydrophobic substance;

the hydrophilic substance is one or more of acrylates, zwitterionic substances, polyethylene glycol substances with different molecular weights, or polyvinylpyrrolidone; the acrylates comprise one or more of 2-hydroxyethyl methacrylate, 2-ethoxyethyl acrylate, and poly(ethylene glycol) methyl ether methacrylate; the zwitterionic substances comprise one or more of 2-methacryloyloxyethyl phosphorylcholine, carboxybetaine, and sulfobetaine; and the hydrophobic substance comprises one or more of lauryl methacrylate, vinyltrimethylsilane, tert-butyl methacrylate, and cyclohexyl methacrylate.

2. The method for constructing the hydrophilic antifouling coating on the surface of the medical implantable material according to claim 1, wherein the medical implantable material comprises polyurethane or silica gel.

3. The method for constructing the hydrophilic antifouling coating on the surface of the medical implantable material according to claim 1, wherein in step 1), the pretreating mode comprises plasma sputtering, ultraviolet irradiation, ozone, washing with a piranha solution, or washing with a sulfuric acid solution; conditions of pretreating with plasma sputtering are as follows: an oxygen atmosphere, and a power of 5-500 W; a condition of pretreating with ultraviolet irradiation is 70 μW/cm²-9 W/cm²; a condition of pretreating with the ozone is 1-100 mg/L; a condition of pretreating with the piranha solution is: concentrated sulfuric acid:hydrogen peroxide=7:3 (v/v); and a condition of pretreating with the sulfuric acid solution is as follows: a mass percentage concentration is 20-80%.

4. The method for constructing the hydrophilic antifouling coating on the surface of the medical implantable material according to claim 1, wherein in step 1), a pretreating time lasts for 1-60 min; and a pretreating temperature is 10-50° C.

5. The method for constructing the hydrophilic antifouling coating on the surface of the medical implantable material according to claim 1, wherein the precursor solution is a silane coupling agent; the silane coupling agent is selected from one or more of KH550, KH570, and KH792;

a mass percentage concentration of the silane coupling agent is 5-60%; a reaction temperature in step 2) is 15-70° C.; and a reaction time in step 2) lasts for 2-8 h.

6. The method for constructing the hydrophilic antifouling coating on the surface of the medical implantable material according to claim 1, wherein in step 4), the washing is performed with one or more of deionized water, ethyl alcohol, and an SDS solution; the drying is forced air drying at a temperature of 20-100° C.; and a mass percentage concentration of the SDS solution is 0.01-1%.

* * * * *

UNITED STATES PATENT AND TRADEMARK OFFICE
CERTIFICATE OF CORRECTION

| | | |
|---|---|---|
| PATENT NO. | : 12,403,223 B2 | Page 1 of 1 |
| APPLICATION NO. | : 18/724324 | |
| DATED | : September 2, 2025 | |
| INVENTOR(S) | : Zhimeng et al. | |

It is certified that error appears in the above-identified patent and that said Letters Patent is hereby corrected as shown below:

In the Specification

In Column 4, Line 15, "--H, --$CH_2$--CH--$CH_2$" should read -- -H, -$CH_2$-CH=$CH_2$--

In Column 4, Line 17, "$R_5$" should read --$R_3$--

In Column 8, Lines 16-17, "--$CH_2$--$CH_2$--CH--$CH_2$" should read -- -$CH_2$-$CH_2$-CH=$CH_2$--

In Column 8, Line 18, "$R_5$" should read --$R_3$--

In the Claims

In Column 19, Claim 1, Lines 14-15, "--H, --$CH_2$--CH--$CH_2$" should read -- -H, -$CH_2$-CH=$CH_2$--

In Column 19, Claim 1, Line 15, "--$CH_2$--$CH_2$--CH--$CH_2$" should read -- -$CH_2$-$CH_2$-CH=$CH_2$--

Signed and Sealed this
Eighteenth Day of November, 2025

John A. Squires
*Director of the United States Patent and Trademark Office*